United States Patent
Lapidus

(10) Patent No.: US 9,284,605 B2
(45) Date of Patent: *Mar. 15, 2016

(54) SINGLE MOLECULE SEQUENCING OF CAPTURED NUCLEIC ACIDS

(71) Applicant: Fluidigm Corporation, South San Francisco, CA (US)

(72) Inventor: Stanley N. Lapidus, Bedford, NH (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/318,104

(22) Filed: Jun. 27, 2014

(65) Prior Publication Data

US 2015/0111204 A1    Apr. 23, 2015

Related U.S. Application Data

(63) Continuation of application No. 12/708,153, filed on Feb. 18, 2010, now Pat. No. 8,802,368, which is a continuation of application No. 11/213,621, filed on Aug. 26, 2005, now Pat. No. 7,666,593.

(51) Int. Cl.
*C12Q 1/68* (2006.01)

(52) U.S. Cl.
CPC .............. *C12Q 1/6869* (2013.01); *C12Q 1/68* (2013.01); *C12Q 1/6874* (2013.01)

(58) Field of Classification Search
None
See application file for complete search history.

(56) References Cited

U.S. PATENT DOCUMENTS 7,666,593 B2 * 2/2010 Lapidus .................. 435/6.12

* cited by examiner

*Primary Examiner* — James Martinell
(74) *Attorney, Agent, or Firm* — Kilpatrick Townsend & Stockton LLP

(57) ABSTRACT

The invention provides methods and devices for detecting, enumerating or identifying target nucleic acid molecules using immobilized capture probes and single molecule sequencing techniques.

5 Claims, No Drawings

SINGLE MOLECULE SEQUENCING OF CAPTURED NUCLEIC ACIDS

TECHNICAL FIELD OF THE INVENTION

This invention relates to methods and compositions for detecting, enumerating, and identifying nucleic acids using capture probes to capture and purify target nucleic acid in combination with single molecule sequencing of the captured or purified nucleic acid molecules.

BACKGROUND OF THE INVENTION

Knowledge of the human genome has given rise to inquiry into individual differences, as well as differences within an individual, as the basis for differences in biological function and dysfunction. Differences as small as single nucleotide polymorphisms (SNPs) or combinations of SNPs can lead to phenotypic differences, and detection of combinations of SNPs can predict the likelihood that an individual will get a specific disease or how an individual will respond to treatment.

For example, most cancers develop from a series of genomic changes, some subtle and some significant, that occur in a small subpopulation of cells. Knowledge of the sequence variations that lead to cancer will lead to an understanding of the etiology of the disease, as well as ways to treat and/or prevent it. An essential first step in understanding genomic complexity is the ability to perform high-resolution sequencing. Therefore, a true understanding of the complexities in either normal or abnormal function will require specific sequence information from large numbers of target nucleic acid molecules.

Bulk sequencing techniques are often not useful for the identification of subtle or rare nucleotide changes due to the many cloning, amplification and electrophoresis steps that complicate the process of gaining useful information regarding individual nucleotides. The ability to sequence and gain information from single molecules obtained from an individual patient is the next milestone for genomic sequencing. However, effective diagnosis and management of important diseases through single molecule sequencing is impeded by lack of cost-effective tools and methods for screening individual molecules.

There have been many proposals to develop new sequencing technologies based on single-molecule measurements, generally either by observing the interaction of particular proteins with DNA or by using ultra high resolution scanned probe microscopy. See, e.g., Rigler, et al., Biotech., 86(3):161 (2001); Goodwin, P. M., et al., Nucleosides & Nucleotides, 16(5-6):543-550 (1997); Howorka, S., et al., Nature Biotech., 19(7):636-639 (2001); Meller, A., et al., Proc. Natl. Acad., 97(3):1079-1084 (2000); Driscoll, R. J., et al., Nature, 346 (6281):294-296 (1990). A recent technique employs optical detection in a sequencing-by-synthesis reaction at the single molecule level. Braslaysky, et al., PNAS, 100: 3960-3964 (2003). The present invention provides improvements in sequencing, especially single molecule sequencing.

SUMMARY OF THE INVENTION

The invention provides methods for sequencing nucleic acids. According to the invention, sequencing is facilitated by capture of target nucleic acids to be sequenced prior to sequencing. In a preferred embodiment, target nucleic acids are sequenced at the single molecule level, resulting in sample-specific, high-throughput sequence information.

Thus, according to one aspect of the invention, sequence-specific capture probes are used to isolate target nucleic acids of interest. The target population may be composed of same-sequence nucleic acids or may be a population of mixed-sequence nucleic acids. The isolated target nucleic acids are then sequenced. In one embodiment, sequencing is performed directly on captured nucleic acids, using the capture probes as primers. Alternatively, target/probe duplex may be melted and the target nucleic acids may then be hybridized to primers for template-dependent sequencing.

In a preferred embodiment, single molecule sequencing is conducted in order to provide high-resolution, high-throughput sequence information. Template-dependent single-molecule sequencing-by-synthesis is conducted using optically-labeled nucleotides for addition to the primer or probe. Either the target (template) or the primer/probe, or both are attached to a surface that is designed to enhance optical signal detection. A particularly-preferred surface is an epoxide surface coated onto glass or fused silica. Nucleic acids are easily attached to epoxide or epoxide derivatives. A preferred method is direct amine attachment. Nucleic acids can be purchased with a 5' or 3' amine, or terminal transferase can be used to introduce a terminal amine for attachment to the epoxide ring. Alternatively, epoxide surfaces can be derivatized for nucleic acid attachment. For example, the surface can incorporate streptavidin, which binds to biotinylated nucleic acids. Either the target, primer/probe, or both can be biotinylated using known methods. Alternative surfaces include polyelectrolyte multilayers as described in Braslavasky, et al., PNAS 100: 3960-64 (2003), incorporated by reference herein. Essentially, any surface that has reduced native fluorescence and is amenable to attachment of oligonucleotides is useful for the invention.

Single molecule sequence is advantageously performed using optically-detectable labels. Especially preferred are fluorescent labels, including fluorescein, rhodamine, derivatized rhodamine dyes, such as TAMRA, phosphor, polymethadine dye, fluorescent phosphoramidite, texas red, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA, or a derivative or modification of any of the foregoing.

The capture step prior to sequencing may be any suitable hybrid capture method. For example, capture can occur in solution, on beads (polystyrene beads), in a column (such as a chromatography column), in a gel (such as a polyacrylamide gel), or directly on the surface to be used for sequencing. An array of support-bound capture oligos can be used to hybridize specifically to a target sequence. Additionally, chromatography-based capture techniques are useful. For example, ion exchange chromatography, HPLC, gas chromatography, and gel-based chromatography all are useful. In one embodiment, gel-based capture is used in order to achieve sequence-specific capture. Using this method, multiple different sequences are captured simultaneously using immobilized probes in the gel. The target sequences are isolated by removing portions of the gel containing them and eluting target from the gel portions for sequencing.

In an alternative embodiment, the target nucleic acid molecule either includes, or is modified to include, an adaptor sequence (such as a polyadenylation region) that is complementary to a portion of a capture probe in order to aid in the capture of the target. A preferred embodiment comprises an immobilized capture probe having a sequence that hybridizes (e.g., is complementary to) with the adaptor sequence. Methods of the invention are conducted by contacting capture probes with a sample comprising target nucleic acid molecules under conditions suitable for specific hybridization between the target nucleic acid molecule and immobilized capture probe, thereby forming target/capture probe duplex. A wash step removes debris and unhybridized nucleic acid in the sample. In one embodiment, target nucleic acid is sequenced using the capture probe as a primer for template-dependent sequencing-by-synthesis. In another embodiment, the target/capture probe duplex is melted to release target nucleic acid. The resulting purified target population is sequenced as described below.

If target nucleic acid is melted off the capture probe, the targets are either attached to a surface for sequencing or hybridized to a primer that has been attached to the surface. Surface attachment of oligonucleotides for sequencing can be direct or indirect. For example, nucleic acids are attached to an epoxide surface via a direct amine linkage as described below. Alternatively, the surface is prepared with a binding partner, the opposite of which is attached to the nucleic acid. For example, the surface can be streptavidinated and biotinylated nucleic acids can be used to form an attachment at the surface. Other binding pairs (e.g., antibody/antigen, such as digoxigenen/anti-digoxigenen and dinitorphenol/anti-dinitrophenol) can also be used.

In a preferred embodiment, the invention contemplates optical sequencing. Preferably, template-dependent sequencing-by-synthesis is conducted using optically-detectable labels. Optimal labels include fluorescent labels as described in detail below. The surface is prepared to minimize background for optical detection of incorporated nucleotides. Primer/template duplex attached to the surface is exposed to labeled nucleoside triphosphates in the presence of a suitable nucleotide polymerizing enzyme, under conditions suitable for the enzyme to add at least one nucleotide to the primer in template-dependent manner, and the added nucleotide is detected, thereby identifying at least one nucleotide in at least one attached target nucleic acid molecule.

As will be appreciated by one skilled in the art, individual features of the invention may be used separately or in any combination. A detailed description of embodiments of the invention is provided below. Other embodiments of the invention are apparent upon review of the detailed description that follows.

DETAILED DESCRIPTION OF THE INVENTION

The present invention provides methods for sequencing nucleic acids. In a preferred embodiment, the invention comprises the use of single molecule sequencing of hybrid-captured nucleic acids. Methods of the invention are highly parallel and are amenable to multiplexing. As a result, biological samples can be rapidly analyzed over a broad dynamic range.

Methods of the invention comprise hybrid-capturing target nucleic acid and sequencing the captured targets. Captured target nucleic acids can be sequenced directly using the capture probe as a primer for template-dependent synthesis. Thus, capture probes are bound to a surface and exposed to sample nucleic acids. Complementary binding of target nucleic acid and probes occurs and the remaining nucleic acid and other sample contents are washed from the surface. Sequencing then takes place essentially as described below. In one alternative, target nucleic acids are isolated by contacting a sample containing target nucleic acid molecules with immobilized capture probes capable of hybridizing to target nucleic acid. Target nucleic acid The surface is washed to remove non-target nucleic acids and other debris, and the targets are then melted off the target/capture probe duplex. After an optional wash, the targets are bound to a surface for sequencing essentially as described below. Target nucleic acid molecules preferably are analyzed using single molecule sequencing techniques described below. In a preferred embodiment, target nucleic acid is modified by addition of a polynucleotide sequence that specifically hybridizes to a complementary portion of a primer for nucleic acid synthesis. For example, targets can be polyadenylated and captured using poly-dT probes/primers for sequencing.

Target Nucleic Acid Molecules

Target nucleic acids include deoxyribonucleic acid (DNA) and/or ribonucleic acid (RNA). Target nucleic acids can be isolated or can be captured in situ. In a preferred alternative, target nucleic acid is isolated from a biological sample containing a variety of other components, such as proteins, lipids and non-target nucleic acids. Target nucleic acid molecules can be obtained from any cellular material, obtained from an animal, plant, bacterium, virus, fungus, or any other cellular organism. Target nucleic acids may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules may also be isolated from cultured cells, such as a primary cell culture or a cell line. The cells from which target nucleic acids are obtained can be infected with a virus or other intracellular pathogen.

A sample can also be total RNA extracted from a biological specimen, a cDNA library, or genomic DNA. Nucleic acid typically is fragmented to produce suitable fragments for capture and/or purification and analysis. In one embodiment, nucleic acid from a biological sample is fragmented by sonication. Test samples can be obtained as described in U.S. Patent Application 2002/0190663 A1, published Oct. 9, 2003, the teachings of which are incorporated herein in their entirety. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, target nucleic acid molecules can be from about 5 bases to about 20 kb. Nucleic acid molecules may be single-stranded, double-stranded, or double-stranded with single-stranded regions (for example, stem-and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$-($OCH_2$-$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Preferred buffer concentration is from about 5 mM to about 500 mM in solution or in solution with the sample. The buffer concentration in the lysing solution can be between about 10 mM and 300 mM.

Subsequent to exposure to a homogenization solution, samples may be further homogenized by mechanical means. Mechanical blenders, rotor-stator homogenizers, or shear-type homogenizers may be employed. Alternatively, the tissue can be homogenized in the lysis solution, and the tissue remains separated by settling, centrifugation, or filtration. These remains could then be treated with homogenization solution and extraction conditions as described above.

Target nucleic acid molecules can include or be modified to include an adaptor sequence that is complementary to the immobilized capture probe. The adaptor sequence and immobilized capture probe are chosen such that the target nucleic acid molecule comprising the adaptor sequence can hybridize to the immobilized capture probe. Typically, the adaptor sequence is a homopolymer, such as oligo(dA), and the corresponding immobilized capture probe includes an oligo(dT) sequence. The adaptor sequence may be endogenously contained within the target nucleic acid molecule, for example, the adaptor sequence can be a sequence of interest in the target nucleic acid molecule. Alternatively, the adaptor sequence can comprise vector sequence.

In one embodiment, a universal probe is used as the immobilized capture probe and the target nucleic acid molecules are modified with an adaptor comprising a sequence complementary to the universal probe, thereby allowing the modified nucleic acid molecules to hybridize to the immobilized probe.

The adaptor sequence and complementary sequence within the immobilized capture probe are of a length suitable for hybridizing the target nucleic acid molecule to the immobilized capture probe to thereby capture target nucleic acid molecules to form target probe/duplexes. The target probe/duplexes are also sufficiently stable to permit optional washing of the duplexes to remove any remaining components of the biological sample, including non-target nucleic acids. The sequence of the adaptor and the complementary sequence of the immobilized capture probe can be about 10 to about 100, and preferably 50, nucleotides in length. The adaptor sequence and complementary immobilized capture sequence can be of the same length or of different lengths. It is routine in the art to adjust probe length and/or oligonucleotide length to optimize hybridization.

The adaptor sequence can be attached to the nucleic acid molecules with an enzyme. The enzyme can be a ligase or a polymerase. The ligase can be an enzyme capable of ligating an oligonucleotide (RNA or DNA) to the nucleic acid molecules. Suitable ligases include, for example, T4 DNA ligase and T4 RNA ligase (such ligases are available commercially, from New England BioLabs (on the World Wide Web at NEB.com). In a preferred embodiment, the target nucleic acid molecules are dephoyshorylated before ligating the adaptors. Methods for using ligases are well known in the art.

The polymerase can be any enzyme capable of adding nucleotides to the target nucleic acid molecules. The polymerase can be, for example, poly(A) polymerase, including yeast poly(A) polymerase, commercially available from USB (on the World Wide Web at USBweb.com), terminal deoxyribonucleotidyl transferase (TdT), and the like. The polymerases can be used according to the manufacturer's instructions.

Purifying Target Nucleic Acid Molecules

As described herein, target nucleic acid molecules can be purified by contacting a sample containing the target molecules with one or more classes of immobilized capture probes. Where more than one target molecule is to be purified, the different target molecules can have the same or different adaptor sequences. A given class of immobilized capture probe is selected to hybridize to target nucleic acid molecules containing the corresponding adaptor sequence, under conditions suitable for the target nucleic acid molecule to hybridize to the immobilized capture probe, thereby forming target/probe duplexes. A variety of capture probes can be used to purify the target nucleic acid molecules. The capture probes typically comprise a nucleic acid with a nucleotide sequence with substantial complementarity to a region of the target nucleic acid molecule, so that the target nucleic acid molecule can hybridize to the capture probe. Complementarity between target nucleic acid molecules and the capture probes need only be sufficient to specifically bind the target nucleic acid molecule, and thus, to effectuate purification of the target nucleic acid molecule from a test sample. Probes suitable for use in the present invention include those formed from nucleic acids, such as RNA and/or DNA, nucleic acid analogues, modified nucleic acids, and chimeric probes of a mixed class comprising a nucleic acid with another organic component such as peptide nucleic acids. Capture probes can be single stranded or double stranded. Preferably, the length of the capture probe is at least 5 nucleotides, more preferably between about 5 and about 100 nucleotides, but the length can be up to several thousand nucleotides. Additional probes are described in U.S. Patent application 2002/0119480 A1, published Aug. 29, 2002, the teachings of which are incorporated herein in their entirety.

Capture probes can be coupled to agarose, dextrans, cellulose, beads, microparticles, and starch polymers using cyanogen bromide or cyanuric chloride activation. Particularly useful beads and microparticles are described in U.S. Patent Application 2003/0190663 A1, published Oct. 9, 2003, the teachings of which are incorporated herein in their entirety. Polymers containing carboxyl groups can be coupled to synthetic capture probes having primary amine groups using carbodiimide coupling. Polymers containing primary amines can be coupled to amine-containing probes with glutaraldehyde or cyanuric chloride. Polymers can also be modified with thiol-reactive groups that can be coupled to thiol-containing probes. Many other suitable methods can be found in the literature (Wong, Chemistry of Protein Conjugation and Cross-Linking, CRC Press, Boca Raton, Fla. 1993). Methods for covalently attaching the capture probes to polymerizable chemical groups are also described in U.S. 2002/0119480A1, the teachings of which are incorporated herein. In addition, as described in U.S. 2002/0119480 A1, nucleic acids can be attached to particles which themselves can be incorporated into electrophoretic media.

To purify target nucleic acid molecules, the test sample can be contacted, for example, with an electrophoretic medium that comprises at least one immobilized capture probe. An electric field is applied across the electrophoretic medium so that negatively charged molecules can migrate through the medium. The non-target components of the test sample pass into the electrophoresis buffer, while the target nucleic acid molecules are captured by hybridizing to the capture probes within the electrophoretic medium (forming target/probe duplexes). The buffer used for the electrophoresis step (containing the non-target components of the test sample) can be replaced with fresh buffer and current applied across the electrophoretic medium to denature the complex, thereby releasing the target nucleic acid molecule from the capture probe. The released target nucleic acid molecule can be eluted by applying a reversed electric field.

The method of the present invention is suitable for multiplexing. As described above, a sample can include more than one target nucleic acid molecule. If adapters are used, the different target nucleic acid molecules can have the same or different adaptor sequences. In a multiplexing reaction, where the target nucleic acid molecules contain different adaptor sequences, the test sample is contacted with two or more classes of immobilized capture probes as described above. Target nucleic acid molecules are captured by their respective immobilized capture probes. The captured target nucleic acid molecules can be released as described above. Other methods for capturing and purifying target nucleic acid molecules are described in U.S. 2002/0119480 A1, the teachings of which are incorporated herein.

Attaching Target Nucleic Acid Molecules to a Surface

In a preferred embodiment, target nucleic acid molecules are attached to a surface and subjected to analysis by single molecules sequencing. Target nucleic acid molecules are attached to the surface such that they are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, filters, or any other structure suitable for anchoring a nucleic acid. Substrates can include planar arrays or matrices capable of having regions that include populations of target nucleic acids or primers. Examples include nucleoside-derivatized CPG and polystyrene slides; derivatized magnetic slides; polystyrene grafted with polyethylene glycol, and the like.

In one embodiment, a substrate is coated to allow optimum optical processing and nucleic acid attachment. Surfaces for use in the invention are treated to reduce background. Exemplary coatings include epoxides, and derivatized epoxides (e.g., with a binding molecule, such as streptavidin). The surface can also be treated to improve the positioning of attached nucleic acids (e.g., target nucleic acid molecules, primers, or target molecule/primer complexes) for analysis. As such, a surface according to the invention can be treated with one or more charge layers (e.g., a negative charge) to repel a charged molecule (e.g., a negatively charged labeled nucleotide). For example, a substrate according to the invention can be treated with polyallylamine followed by polyacrylic acid to form a polyelectrolyte multilayer. The carboxyl groups of the polyacrylic acid layer are negatively charged and thus repel negatively charged labeled nucleotides, improving the positioning of the label for detection.

Coatings or films applied to the substrate should be able to withstand subsequent treatment steps (e.g., photoexposure, boiling, baking, soaking in warm detergent-containing liquids, and the like) without substantial degradation or disassociation from the substrate.

Examples of substrate coatings include, vapor phase coatings of 3-aminopropyltrimethoxysilane, as applied to glass slide products, for example, from Molecular Dynamics, Sunnyvale, Calif. In addition, generally, hydrophobic substrate coatings and films aid in the uniform distribution of hydrophilic molecules on the substrate surfaces. Importantly, in those embodiments of the invention that employ substrate coatings or films, the coatings or films that are substantially non-interfering with primer extension and detection steps are preferred. Additionally, it is preferable that any coatings or films applied to the substrates either increase target molecule binding to the substrate or, at least, do not substantially impair target binding.

Various methods can be used to anchor or immobilize the target nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mole. Bio. Rep. 11:107-115, 1986. A preferred attachment is direct amine bonding of a terminal nucleotide to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et aL, Science 253: 1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to supports also can be used.

In a preferred embodiment, surfaces for oligonucleotide attachment are coated with an epoxide. An epoxide may be deposited by many methods known in the art. An epoxy silane surface is preferred. Different molecules or combinations of molecules may serve to link the epoxide to a surface. Ideally, a surface will be coated with an even distribution of epoxides prior to introduction of target nucleic acid molecules. Target nucleic acid molecules can be directly or indirectly linked to an epoxide. In a direct attachment embodiment, the epoxide is introduced to a nucleic acid bearing an amine group. In a preferred embodiment, terminal transferase is used to add an amine-terminated nucleotide to a nucleic acid to be attached to the surface.

When biotin-streptavidin linkage is used to anchor the nucleic acids, the nucleic acids can be biotinylated, while one surface of the substrates can be coated with streptavidin.

Surface density of the nucleic acid molecules can be controlled by adjusting the concentration of the streptavidin applied to the surface. Reagents for biotinylating a surface can be obtained, for example, from Vector Laboratories. Alternatively, biotinylation can be performed with BLCPA: EZ-Link Biotin LC-PEO-Amine (Pierce, Cat. 21347), or any other known or convenient method. In some embodiments, labeled streptavidin of very low concentration (e.g., in the µM, nM or pM range) is used to coat the substrate surface prior to anchoring. This can facilitate immobilization of the nucleic acid with single molecule resolution.

Other examples of linkers include antigen/antibody, digoxigenin/anti-digoxigenin, dinitrophenol, fluorescein, and other haptens known in the art. Alternatively, the nucleic acid may contain other binding moieties that result in a conformational change of the epoxide ring and result in a direct attachment of the target nucleic acid molecules to the opened epoxide ring.

Alternatively, primers may be immobilized on the surface. A terminus of one or more primers may be modified to carry a linker moiety for tethering the primers to the surface or may be directly attached to the surface. Target nucleic acid molecules containing primer complementary sequence are then hybridized to the attached primer. Methods for attaching nucleic acid such as primer to the surface of a substrate are described in detail above.

In order to inhibit non-specific binding of molecules to a surface, the surface can be treated with a passivating (blocking) agent. Preferred blocking strategies include exposing the surface to a non-detectable molecule that adheres to the surface or changes the chemical properties of the surface such that non-specific binding is reduced. In methods in which optically-detectable labels are used, one way to block or passivate the surface is to expose the surface to unlabeled molecules of the same type as those that are labeled. The unlabeled molecules will out-compete labeled molecules for non-specific binding on the surface, thus reducing background due to non-specific label. Other strategies involve treating the surface with phosphate, Tris, a sulfate, or an amine that interacts with the surface to prevent non-specific binding. Non-reactive proteins are also appropriate. In a preferred embodiment, a matrix of blocking reagents is provided on the surface in order to provide a highly washable, low non-specific background surface. In some embodiments, blocking reagents are chosen to provide electrostatic repulsion of highly anionic nucleoside triphosphates.

Blocking agents may be introduced or reintroduced at any time during the analysis. Also, in some embodiments, blocking agents may be used to pre-treat the surface prior to exposing the substrate to target nucleic acid molecules or primers. In addition, blocking agents, such as a detergent (e.g., Tris) may be included in some or all wash steps in order to passivate the surface during incubation periods and/or washes.

Surface charge can be manipulated to achieve ideal conditions during both nucleic acid attachment and primer extension. For example, during the loading phase where the nucleic acid (target nucleic acid molecule or primer) is bound to the surface, the salt concentration of the solution may be increased in order to create a more positive surface charge on the substrate to facilitate reaction between the amine portion of the nucleic acid and the epoxide ring. Conversely, after the nucleic acid has been secured to the surface, the salt concentration of the solution can lowered in order to repel the nucleic acid from the surface of the substrate thereby sterically conforming the nucleic acid for annealing and sequence analysis.

In another embodiment, the substrate includes a layer of polyanions and nucleic acid molecules anchored on the layer of polyanions. Accordingly, nucleic acids are positioned to avoid being substantially parallel (e.g., is hindered from lying down on the layer of polyanions.) In some embodiments, the surface of a substrate is pretreated to create a surface chemistry that facilitates nucleic acid attachment and subsequent annealing and sequence analysis. In some of these embodiments, the substrate surface is coated with a polyelectrolyte multilayer (PEM). In some cases, biotin can be applied to the PEM, followed by application of streptavidin. The substrate can then be used to attach biotinylated target nucleic acid molecules.

In some embodiments, multiple layers of alternating positive and negative charges are used. In the case of incompletely-charged surfaces, multiple-layer deposition tends to increase surface charge to a well-defined and stable level. For example, surfaces can be coated with a PEM for attachment of primers via light-directed spatial attachment. Alternatively, target nucleic acid molecules can be attached to a PEM-coated surface chemically. PEM formation has been described in Decher et al. (Thin Solid Films, 210:831-835, 1992), the teachings of which are incorporated herein. PEM formation proceeds by the sequential addition of polycations and polyanions, which are polymers with many positive or negative charges, respectively. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to poly(+) and poly(-) generates a polyelectrolyte multilayer structure with a surface charge determined by the last polyelectrolyte added. This can produce a strongly-negatively-charged surface, repelling the negatively-charged nucleotides. Detailed procedures for coating a substrate with PEM for immobilizing nucleic acid are described in U.S. patent application Ser. No. 11/137,928, field May 25, 2005.

In another aspect of the invention, the substrate may be prepared by, for example, coating with a chemical that increases or decreases hydrophobicity or coating with a chemical that allows covalent linkage of the primers. Some chemical coatings may both alter the hydrophobicity and allow covalent linkage. Hydrophobicity on a solid substrate may readily be increased by silane treatment or other treatments known in the art. Linker molecules adhere to the surface and comprise a functional moiety that reacts with biomolecules. Many such linkers are readily available and known in the art. For example, substrates or supports are modified with photolabile-protected hydroxyl groups, alkoxy or aliphatic derivatized hydroxyl groups, or other chemicals. A preferred coating that both decreases hydrophobicity and provides linkers is poly(ethyleneimine).

Methods of the invention also optionally include a surface drying step. In some embodiments, the surface is exposed to a drying agent prior to, during and/or after a chemical reaction, such as a nucleotide incorporation step. Examples of preferred drying agents include, without limitation, phosphate buffer, an alcohol (such as, for example, EtOH), air and/or $N_2$.

Analyzing Attached Target Nucleic Acid Molecules

As described herein, attached target nucleic acid molecules are analyzed by single molecule sequencing. At least one nucleotide is identified in at least one attached target nucleic acid molecule. Target molecules are hybridized to a primer to form nucleic acid target molecule/primer duplex on a surface. As described above, either the target nucleic acid molecule or the primer, or both, is/are attached to the surface. Thereafter, template-dependent primer extension is conducted to identify at least one nucleotide of the hybridized nucleic acid molecule using a nucleotide polymerizing enzyme and a nucleotide (e.g., dATP, dTTP, dUTP, dCTP and/or a dGTP) or a nucleotide analog. Incorporation of a nucleotide or a nucleotide analog is detected at discrete locations on the surface. Nucleic acid target molecule/primer duplexes, as well as the incorporated nucleotides, are individually resolvable in single molecule embodiments. Alternatively, bulk signal from mixed nucleic acid populations or clonal populations of nucleic acids, are obtained.

Fast reagent application and removal is another advantage of the invention. For example, concentrations of nucleotides and/or other reaction reagents can be alternated at different time points. This is a particularly useful feature in an embodiment comprising introducing one or more single species of nucleotide individually. This could lead to increased incorporation rates and sensitivity. For example, when all four types of nucleotides are simultaneously present in the reaction to monitor dynamic incorporation of nucleotides, concentrations of the each of the respective nucleotides can be alternated between a first and a second range. This leads to both better visualization of the signal when low concentrations of nucleotides are present, and increased polymerization rate when higher concentrations of nucleotides are present.

The target nucleic acid can comprise or can be modified to comprise a sequence that is sufficiently complementary to a primer to hybridize to the primer to allow template dependent addition of nucleotides to the hybridized primer. The sequence complementary to the primer can be the same as the previously described adaptor sequence. Therefore, the immobilized capture probe and the primer can comprise the same sequence. The primer sequence can be about 10 to about 1000 nucleotides in length. The primer sequence and complementary target nucleic acid molecule sequence can be of the same length or of different lengths. Conditions for hybridizing primers to nucleic acid targets are well known. The annealing reaction is performed under conditions which are stringent enough to guarantee sequence specificity, yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium. Typically, hybridization (annealing) between primers and target nucleic acids is carried out at a temperature that is approximately 5 to 10° C. below the melting temperature of the target-primer hybrid in the annealing solvent. Typically, the annealing temperature is in the range of 55 to 75° C. and the primer concentration is approximately 0.2 µM. Under such conditions, the annealing reaction is usually complete within a few seconds.

Methods according to the invention include conducting a primer extension reaction, such as exposing the nucleic acid/primer complexes to polymerase and one or more nucleotides under conditions sufficient to extend the primer by at least one base. Sequencing, as used herein can be performed such that one or more nucleotides are identified in one or more nucleic molecules. Methods according to the invention also include the step of compiling a sequence of the molecule (nucleic acid) based upon sequential incorporation of the extension bases into the primer.

In the analyzing step, the hybridized nucleic acid molecules can be sequenced using single molecule sequencing as described, for example, in U.S. patent application Ser. No. 11/137,928, filed May 25, 2005 and/or and described in U.S. Pat. No. 6,780,591, the teachings of which are incorporated herein in their entirety. Polymerases useful in the invention include any nucleic acid polymerase capable of catalyzing a template-dependent addition of a nucleotide or nucleotide analog to a primer. Depending on the characteristics of the target nucleic acid, a DNA polymerase, an RNA polymerase, a reverse transcriptase, or a mutant or altered form of any of the foregoing can be used. According to one aspect of the invention, a thermophilic polymerase is used, such as ThermoSequenase®, 9°N™, Therminator™, Taq, Tne, Tma, Pfu, Tfl, Tth, Tli, Stoffel fragment, Vent™ and Deep Vent™ DNA polymerase.

The target nucleic acid molecule/primer complexes are contacted with dNTPs in the presence of the polymerase under conditions such that the polymerase catalyzes template-dependent addition of a dNTP to the 3' terminus of the primer. The dNTP can be detectably labeled, as described herein, and the nucleotide is identified by detecting the presence of the incorporated labeled nucleotide. As described above, unincorporated labeled dNTPs can be removed from the surface prior to detecting the incorporated labeled dNTP. The process can be repeated one or more times, wherein the template/primer complex(es) are provided with additional dNTPs, in the presence of a polymerase, followed by removing the unincorporated labeled dNTPs and detecting the incorporated labeled dNTP. The sequence of the template is determined by compiling the detected (identified) dNTPs. In this manner, the entire sequence of one or more templates can be determined. In addition, by using single molecule sequencing techniques, determining the sequence for each nucleic acid molecule attached to the surface provides the number of different or unique nucleic acid molecules in the sample. Furthermore, the number of copies of each nucleic acid sequences in a biological sample is also provided.

In order to allow for further extension and detection of subsequently added fluorophore-labeled nucleotides, the fluorophore of the incorporated nucleotide can be removed from the nucleotide incorporated into the primer. For example, the optical label (e.g., fluorescent label) can be destroyed by photochemical destruction as described in U.S. Pat. No. 6,780,591, the teachings of which are incorporated herein in their entirety. This cycle can be repeated a large number of times if sample losses are avoided. In one embodiment, such losses will be avoided by attaching the target nucleic acid molecules or primers to a surface of an array device, for example a microscope slide, and transferring the entire array device between a reaction vessel and the fluorescent reader.

The extension reactions are carried out in buffer solutions which contain the appropriate concentrations of salts, dNTP(s) and nucleotide polymerizing enzyme required for the enzyme mediated extension to proceed. For additional guidance regarding such conditions see, for example, Sambrook et al., (1989, Molecular Cloning, A Laboratory Manual, Cold Spring Harbor Press, NY); and Ausubel et al. (1989, Current Protocols in Molecular Biology, Green Publishing Associates and Wiley Interscience, NY).

Nucleotides particularly useful in the invention comprise detectable labels. Labeled nucleotides include any nucleotide that has been modified to include a label that is directly or indirectly detectable. Preferred labels include optically-detectable labels, including fluorescent labels or fluorophores, such as fluorescein, rhodamine, cyanine, cyanine-5 dye, cyanine-3 dye, or a derivative or modification of any of the foregoing, and also include such labeling systems as hapten labeling. Accordingly, methods of the invention further provide for exposing the primer/target nucleic acid complex to a digoxigenin, a fluorescein, an alkaline phosphatase or a peroxidase.

The sequencing can be optimized to achieve rapid and complete addition of the correct nucleotide to primers in primer/template complexes, while limiting the misincorporation of incorrect nucleotides. For example, dNTP concentrations may be lowered to reduce misincorporation of incorrect nucleotides into the primer. $K_m$ values for incorrect dNTPs can be as much as 1000-fold higher than for correct nucleotides, indicating that a reduction in dNTP concentrations can reduce the rate of misincorporation of nucleotides. Thus, in a preferred embodiment of the invention the concentration of dNTPs in the sequencing reactions are approximately 5-20 µM.

In addition, relatively short reaction times can be used to reduce the probability of misincorporation. For an incorporation rate approaching the maximum rate of about 400 nucleotides per second, a reaction time of approximately 25 milliseconds will be sufficient to ensure extension of 99.99% of primer strands.

Detection

Any detection method may be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T.G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached target nucleic acids.

The present invention provides for detection of molecules from a single nucleotide to a single target nucleic acid molecule. A number of methods are available for this purpose. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified COD camera also can be used. Additionally, low noise cooled CCD can also be used to detect single fluorescent molecules.

The detection system for the signal may depend upon the labeling moiety used, which can be defined by the chemistry available. For optical signals, a combination of an optical fiber or charged couple device (CCD) can be used in the detection step. In those circumstances where the substrate is itself transparent to the radiation used, it is possible to have an incident light beam pass through the substrate with the detector located opposite the substrate from the target nucleic acid. For electromagnetic labeling moieties, various forms of spectroscopy systems can be used. Various physical orientations for the detection system are available and discussion of important design parameters is provided in the art.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for two-dimensional imaging. TIRF microscopy uses totally internally reflected excitation light and is well known in the art. See, e g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached target nucleic acid target molecule/primer complex in the presence of a polymerase. Total internal reflectance fluorescence microscopy is then used to visualize the attached target nucleic acid target molecule/primer complex and/or the incorporated nucleotides with single molecule resolution.

Measured signals can be analyzed manually or by appropriate computer methods to tabulate results. The substrates and reaction conditions can include appropriate controls for verifying the integrity of hybridization and extension conditions, and for providing standard curves for quantification, if desired. For example, a control nucleic acid can be added to the sample. The absence of the expected extension product is an indication that there is a defect with the sample or assay components requiring correction.

Fluorescence resonance energy transfer (FRET) can be used as a detection scheme. FRET in the context of sequencing is described generally in Braslavasky, et al., Proc. Nat'l Acad. Sci., 100: 3960-3964 (2003), incorporated by reference herein. Essentially, in one embodiment, a donor fluorophore is attached to the primer, polymerase, or template. Nucleotides added for incorporation into the primer comprise an acceptor fluorophore that is activated by the donor when the two are in proximity.

As described herein, combination articles of manufacture are provided that are suitable for performing the method of the invention. Suitable surfaces are described above. The enzyme can be a ligase or a polymerase, as described above. The adaptor sequence can optionally comprise a linker moiety at the 5' terminus of the adaptor sequence, the linker moiety being suitable for attaching a target molecule to the surface. Other suitable linker moieties are described above.

EXAMPLE

The 7249 nucleotide genome of the bacteriophage M13mp18 was sequenced using a single molecule system of the invention. Purified, single-stranded viral M13mp18 genomic DNA was obtained from New England Biolabs. Approximately 25 ug of M13 DNA was digested to an average fragment size of 40 bp with 0.1 U Dnase I (New England Biolabs) for 10 minutes at 37° C. Digested DNA fragment sizes were estimated by running an aliquot of the digestion mixture on a precast denaturing (TBE-Urea) 10% polyacrylamide gel (Novagen) and staining with SYBR Gold (Invitrogen/Molecular Probes). The DNase I-digested genomic DNA was filtered through a YM10 ultrafiltration spin column (Millipore) to remove small digestion products less than about 30 nt. Approximately 20 pmol of the filtered DNase I digest was then polyadenylated with terminal transferase according to known methods (Roychoudhury, R and Wu, R. 1980, Terminal transferase-catalyzed addition of nucleotides to the 3' termini of DNA. Methods Enzymol. 65(1):43-62.). The average dA tail length was 50+/−5 nucleotides. Terminal transferase was then used to label the fragments with Cy3-dUTP. Fragments were then terminated with dideoxyTTP (also added using terminal transferase). The resulting fragments were again filtered with a YM10 ultrafiltration spin column to remove free nucleotides and stored in ddH2O at −20° C.

Epoxide-coated glass slides were prepared for oligo attachment. Epoxide-functionalized 40 mm diameter #1.5 glass cover slips (slides) were obtained from Erie Scientific (Salem, N.H.). The slides were preconditioned by soaking in 3×SSC for 15 minutes at 37° C. Next, a 500 pM aliquot of 5' aminated polydT(50) (polythymidine of 50 bp in length with a 5' terminal amine) was incubated with each slide for 30 minutes at room temperature in a volume of 80 ml. The resulting slides had poly(dT50) primer attached by direct amine linkage to the epoxide. The slides were then treated with phosphate (1M) for 4 hours at room temperature in order to passivate the surface. Slides were then stored in polymerase rinse buffer (20 mM Tris, 100 mM NaCl, 0.001% Triton X-100, pH 8.0) until they were ready for sequencing.

For sequencing, the slides were placed in a modified FCS2 flow cell (Bioptechs, Butler, Pa.) using a 50 um thick gasket. The flow cell was placed on a movable stage that is part of a high-efficiency fluorescence imaging system built around a Nikon TE-2000 inverted microscope equipped with a total internal reflection (TIR) objective. The slide was then rinsed with HEPES buffer with 100 mM NaCl and equilibrated to a temperature of 50° C. An aliquot of the M13 template fragments described above was diluted in 3×SSC to a final concentration of 1.2 nM. A 100 ul aliquot was placed in the flow cell and incubated on the slide for 15 minutes. After incubation, the flow cell was rinsed with 1×SSC/HEPES/0.1% SDS followed by HEPES/NaCl. A passive vacuum apparatus was used to pull fluid across the flow cell. The resulting slide contained M13 template/oligo(dT) primer duplex. The temperature of the flow cell was then reduced to 37° C. for sequencing and the objective was brought into contact with the flow cell.

For sequencing, cytosine triphosphate, guanidine triphosphate, adenine triphosphate, and uracil triphosphate, each having a cyanine-5 label (at the 7-deaza position for ATP and GTP and at the C5 position for CTP and UTP (PerkinElmer)) were stored separately in buffer containing 20 mM Tris-HCl, pH 8.8, 10 mM $MgSO_4$, 10 mM $(NH_4)_2SO_4$, 10 mM HCl, and 0.1% Triton X-100, and 100U Klenow exo⁻ polymerase (NEN). Sequencing proceeded as follows.

First, initial imaging was used to determine the positions of duplex on the epoxide surface. The Cy3 label attached to the M13 templates was imaged by excitation using a laser tuned to 532 nm radiation (Verdi V-2 Laser, Coherent, Inc., Santa Clara, Calif.) in order to establish duplex position. For each slide only single fluorescent molecules were imaged in this step were counted. Imaging of incorporated nucleotides as described below was accomplished by excitation of a cyanine-5 dye using a 635 nm radiation laser (Coherent). 5 uM Cy5CTP was placed into the flow cell and exposed to the slide for 2 minutes. After incubation, the slide was rinsed in 1×SSC/15 mM HEPES/0.1% SDS/pH 7.0 ("SSC/HEPES/SDS") (15 times in 60ul volumes each, followed by 150 mM HEPES/150 mM NaCl/pH 7.0 ("HEPES/NaCl") (10 times at 60 ul volumes). An oxygen scavenger containing 30% acetonitrile and scavenger buffer (134 ul HEPES/NaCl, 24 ul 100 mM Trolox in MES, pH 6.1, 10 ul DABCO in MES, pH6.1, 8ul 2M glucose, 20 ul NaI (50 mM stock in water), and 4ul glucose oxidase) was next added. The slide was then imaged (500 frames) for 0.2 seconds using an Inova301K laser (Coherent) at 647 nm, followed by green imaging with a Verdi V-2 laser (Coherent) at 532 nm for 2 seconds to confirm duplex position. The positions having detectable fluorescence were recorded. After imaging, the flow cell was rinsed 5 times each with SSC/HEPES/SDS (60ul) and HEPES/NaCl (60ul). Next, the cyanine-5 label was cleaved off incorporated CTP by introduction into the flow cell of 50 mM TCEP for 5 minutes, after which the flow cell was rinsed 5 times each with SSC/HEPES/SDS (60ul) and HEPES/NaCl (60ul). The remaining nucleotide was capped with 50 mM iodoacetamide for 5 minutes followed by rinsing 5 times each with SSC/HEPES/SDS (60ul) and HEPES/NaCl (60ul). The scavenger was applied again in the manner described above, and the slide was again imaged to determine the effectiveness of the cleave/cap steps and to identify non-incorporated fluorescent objects.

The procedure described above was then conducted 100 nM Cy5dATP, followed by 100 nM Cy5dGTP, and finally 500 nM Cy5dUTP. The procedure (expose to nucleotide, polymerase, rinse, scavenger, image, rinse, cleave, rinse, cap, rinse, scavenger, final image) was repeated exactly as described for ATP, GTP, and UTP except that Cy5dUTP was incubated for 5 minutes instead of 2 minutes. Uridine was used instead of thymidine due to the fact that the Cy5 label was incorporated at the position normally occupied by the methyl group in Thymidine triphosphate, thus turning the dTTP into dUTP. In all 64 cycles (C, A, G, U) were conducted as described in this and the preceding paragraph.

Once 64 cycles were completed, the image stack data (i.e., the single molecule sequences obtained from the various surface-bound duplex) were aligned to the M13 reference sequence. The image data obtained was compressed to collapse homopolymeric regions. Thus, the sequence "TCAAAGC" would be represented as "TCAGC" in the data tags used for alignment. Similarly, homopolymeric regions in the reference sequence were collapsed for alignment. The sequencing protocol described above resulted in an aligned M13 sequence with an accuracy of between 98.8% and 99.96% (depending on depth of coverage). The individual single molecule sequence read lengths obtained ranged from 2 to 33 consecutive nucleotides with about 12.6 consecutive nucleotides being the average length.

The alignment algorithm matched sequences obtained as described above with the actual M13 linear sequence. Placement of obtained sequence on M13 was based upon the best match between the obtained sequence and a portion of M13 of the same length, taking into consideration 0, 1, or 2 possible errors. All obtained 9-mers with 0 errors (meaning that they exactly matched a 9-mer in the M13 reference sequence) were first aligned with M13. Then 10-, 11-, and 12-mers with 0 or 1 error were aligned. Finally, all 13-mers or greater with 0, 1, or 2 errors were aligned. At a coverage depth of greater than or equal to 1, 5,001 bases of the 5,066 base M13 collapsed genome were covered at an accuracy of 98.8%. Similarly, at a coverage depth of greater than or equal to 5, 83.6% of the genome was covered at an accuracy of 99.3%, and at a depth of greater than or equal to 10, 51.9% of the genome was covered at an accuracy of 99.96%. The average coverage depth was 12.6 nucleotides.

I claim:

1. A method for obtaining sequence information from a selected nucleic acid, the method comprising the steps of:
   capturing target nucleic acids with a sequence-specific capture probes to produce a plurality of target/probe duplexes, wherein the target nucleic acids comprise RNA;
   melting the target/probe duplexes to release target nucleic acids;
   annealing primers to released target nucleic acids to produce target/primer duplexes;
   introducing a polymerase and at least one nucleotide species comprising an optically-detectable label under conditions sufficient for template-dependent nucleotide addition to said primer;
   removing unincorporated nucleotides;
   identifying nucleotide species incorporated into said primer, thereby obtaining sequence information from said target nucleic acids.

2. The method according to claim 1, wherein the optically detectably labeled nucleotide is fluorescently labeled nucleotide.

3. The method according to claim 1, wherein the target nucleic acids comprise adaptor sequences.

4. The method according to claim 3, wherein different target nucleic acids have the same or different adaptor sequences.

5. The method of claim 1 wherein the probes are a plurality of different sequence-specific probes.

* * * * *